US011202894B1

(12) United States Patent
Thau et al.

(10) Patent No.: US 11,202,894 B1
(45) Date of Patent: Dec. 21, 2021

(54) RECLOSEABLE SWAB APPLICATOR

(71) Applicants: Howard Thau, Woodcliff Lake, NJ (US); Thomas Nagler, Greenlawn, NY (US); Michael A Botta, Ridge, NY (US); Mian S Yousuf, Bay Shore, NY (US)

(72) Inventors: Howard Thau, Woodcliff Lake, NJ (US); Thomas Nagler, Greenlawn, NY (US); Michael A Botta, Ridge, NY (US); Mian S Yousuf, Bay Shore, NY (US)

( * ) Notice: Subject to any disclaimer, the term of this patent is extended or adjusted under 35 U.S.C. 154(b) by 763 days.

(21) Appl. No.: 15/602,095

(22) Filed: May 22, 2017

(51) Int. Cl.
| *A61M 35/00* | (2006.01) |
| *A61F 13/36* | (2006.01) |
| *A61F 13/38* | (2006.01) |
| *A61F 13/40* | (2006.01) |
| *A61F 13/15* | (2006.01) |

(52) U.S. Cl.
CPC ........... *A61M 35/006* (2013.01); *A61F 13/36* (2013.01); *A61F 13/38* (2013.01); *A61F 2013/15008* (2013.01); *A61M 35/00* (2013.01); *A61M 35/003* (2013.01)

(58) Field of Classification Search
CPC .. A61M 35/00; A61M 35/006; A61M 35/003; A61F 13/36; A61F 13/38; A61F 2013/15008
See application file for complete search history.

(56) References Cited

U.S. PATENT DOCUMENTS

571,367 A * 11/1896 Higgins
3,818,911 A 6/1974 Fournier
(Continued)

Primary Examiner — Tatyana Zalukaeva
Assistant Examiner — Ilya Y Treyger
(74) Attorney, Agent, or Firm — Chinta & Fratangelo LLP (57) ABSTRACT

An improved two-part swab applicator is provided, having a handle section and a receptacle section that are engaged through coupling and an end cap. A stem having a swab attached at one end is encompassed by both sections with the swab nesting within the receptacle section. The receptacle section has a hollow body and a plurality of ribs on the body to prevent the applicator from rolling and the liquid from spilling. The receptacle section may also have a collar with one or more notches to prevent rolling of the receptacle section. The end cap may have a collar with one or more notches that prevent the handle section and/or the applicator from rolling and catches any drips of the liquid when the swab is removed for use. The end cap also has a plurality of ribs on its body that prevents the applicator from rolling. The handle and receptacle sections nest in each other with a snug fit and mate and decouple with a twisting or rotating action of the end cap that also serves as a drip shield preventing the liquid from dripping. When connected, any liquid contained in the receptacle section is securely air sealed by the snug contact of the receptacle and handle sections. The swab may be impregnated with a medicine or liquid. Alternatively, the swab may be sterile and is used to collect a tissue or excretion sample from humans or animals. After use, the swab may be returned to the receptacle section and the air-tight seal reformed for sanitary disposal or further transport for analysis of the collected sample. The swab may be used on an exterior part or body cavity of a human or an animal.

20 Claims, 8 Drawing Sheets

(56) References Cited

U.S. PATENT DOCUMENTS

| | | | |
|---|---|---|---|
| 3,918,435 A * | 11/1975 | Beall | A61B 10/0096 |
| | | | 600/572 |
| 3,923,604 A | 12/1975 | Monaghan | |
| 4,747,719 A | 5/1988 | Parkin | |
| 4,952,204 A | 8/1990 | Korteweg | |
| 5,316,399 A | 5/1994 | Joulia | |
| 5,511,654 A | 4/1996 | de la Rocha | |
| 6,406,451 B1 | 6/2002 | Rowe | |
| 7,337,907 B2 | 3/2008 | Shah | |
| 9,427,361 B2 | 8/2016 | Buell et al. | |
| 2006/0095000 A1 | 5/2006 | Kimmell | |
| 2008/0292383 A1* | 11/2008 | Tufts | A45D 34/04 |
| | | | 401/133 |

\* cited by examiner

RECLOSEABLE SWAB APPLICATOR

FIELD OF THE INVENTION

The present invention relates generally to swab applicators. More particularly, the invention relates to an improved disposable prepackaged swab applicator for applying liquids such as medicines or to collect a tissue sample or excretion.

BACKGROUND

Currently, a number of disposable applicators for various purposes such as application of medicines, cosmetics or cleaning are well known. Prepackaged applicators that contain a preselected amount of liquid for a single application are also known. Such applicators typically contain a sterile swab housed within various forms of a protective casing or packaging. For example, U.S. Pat. No. 3,818,911 to Fournier discloses a swab contained within a housing that can be used to deliver a medicament to a body cavity such as the vagina. Some of the self-contained swab applicators, such as those disclosed in U.S. Pat. Nos. 4,952,204 and 6,406,451 B1, come with a sealed reservoir storing a liquid that is punctured or compressed at the time of use.

In spite of significant level of activity directed to prepackaged swab applicators, known applicators are characterized by their lack of adequate protection especially upon opening the applicator for use. Applicators typically come as a single piece that is either punctured off or ruptured or compressed at a certain point along the body of the applicator to expose the swab for use. Applicators with liquid contained in foil patches get messy upon opening. Applicators with liquid contained in plastic tubes are also messy when broken open for use. Once the reservoir containing the liquid is opened, the medicine spills out of the reservoir or the reservoir rolls out when put on a flat surface such as a table. Additionally, once the swab is removed from an applicator assembly, it is hard to put it back and reseal presenting contamination issues. Present applicators also do not provide a good air-tight seal.

Accordingly, there is a need for an improved swab applicator that overcomes these drawbacks and is easy, compact, and safe to use and dispose.

SUMMARY OF THE INVENTION

The present invention addresses these shortcomings by providing an improved swab applicator. In an embodiment, the improved swab applicator is prepackaged, sealed, openable, and comprises two detachable sections, a handle section and a receptacle section. The handle section includes a swab, a stem, and a handle comprising an end cap that serves as a drip shield and acts as a connector between the two sections. The end cap connects and engages the two sections by threads or other suitable means that provides force to keep the two sections in contact with one another. The receptacle section comprises a generally tapered hollow body and a neck with threads or other suitable means adapted to connect with the end cap on the handle section. An airtight seal is formed between the hollow body of the receptacle section and the mating portion of the handle section. The body of the receptacle section has elevating ribs that prevents spills and rolls. The handle section also has elevating ribs. The handle and/or the receptacle sections also have a collar with notches and feet to prevent rolling. Alternately, the anti-roll and anti-spill features may be accomplished by the cross-sectional shape of the receptacle section and/or the handle section.

The receptacle section may be packaged with a liquid such as a medicine or pharmaceutical composition that impregnates the swab for delivery to the exterior of a human or animal, or for delivery to a body cavity of a human or animal. The swab may also be used to collect a tissue sample or excretion from the exterior of the body of a patient or from a body cavity of a human or animal. After use, the swab may be inserted back into the receptacle section re-forming the air-tight seal and the receptacle section and handle section securely coupled with the end cap.

DETAILED DESCRIPTION OF THE INVENTION

The following detailed description and accompanying drawings disclose various aspects and/or embodiments of the invention. Alternate aspects and/or embodiments may be devised without departing from the scope of the disclosure. Additionally, well-known elements of the disclosure are not described in detail or have been omitted so as not to obscure the relevant details of the disclosure.

Any aspect or embodiment described herein as "exemplary," "such as," and/or "example" is not necessarily to be construed as preferred or advantageous over other aspects or embodiments. Likewise, the term "aspect/embodiment of the disclosure/invention" does not require that all aspects or embodiments include the discussed feature, advantage or mode of operation.

An improved swab applicator is disclosed having a swab, a stem attached to the swab on one end, and an applicator assembly for encapsulating the swab and the stem that can be opened and closed. The applicator assembly comprises a handle section and a hollow receptacle section. The handle section includes an end cap that serves as a drip shield to prevent dripping. The end cap comprises a body having a plurality of elevating ribs to aid gripping and avoid rolling by keeping the applicator elevated when resting on a flat surface. The end cap houses the other end of the stem in a stem seat and there is a female thread on the interior side of the end cap body. The receptacle section comprises a tapered hollow body with a narrow closed end and a wider open end, wherein the open end has a neck and a rim having male screw thread lugs adapted to mate or couple with the female screw threads on the end cap body. The body of the receptacle section has a plurality of elevating ribs that keep the receptacle section elevated when resting on a flat surface and prevent spilling and rolling.

Figure 1A:
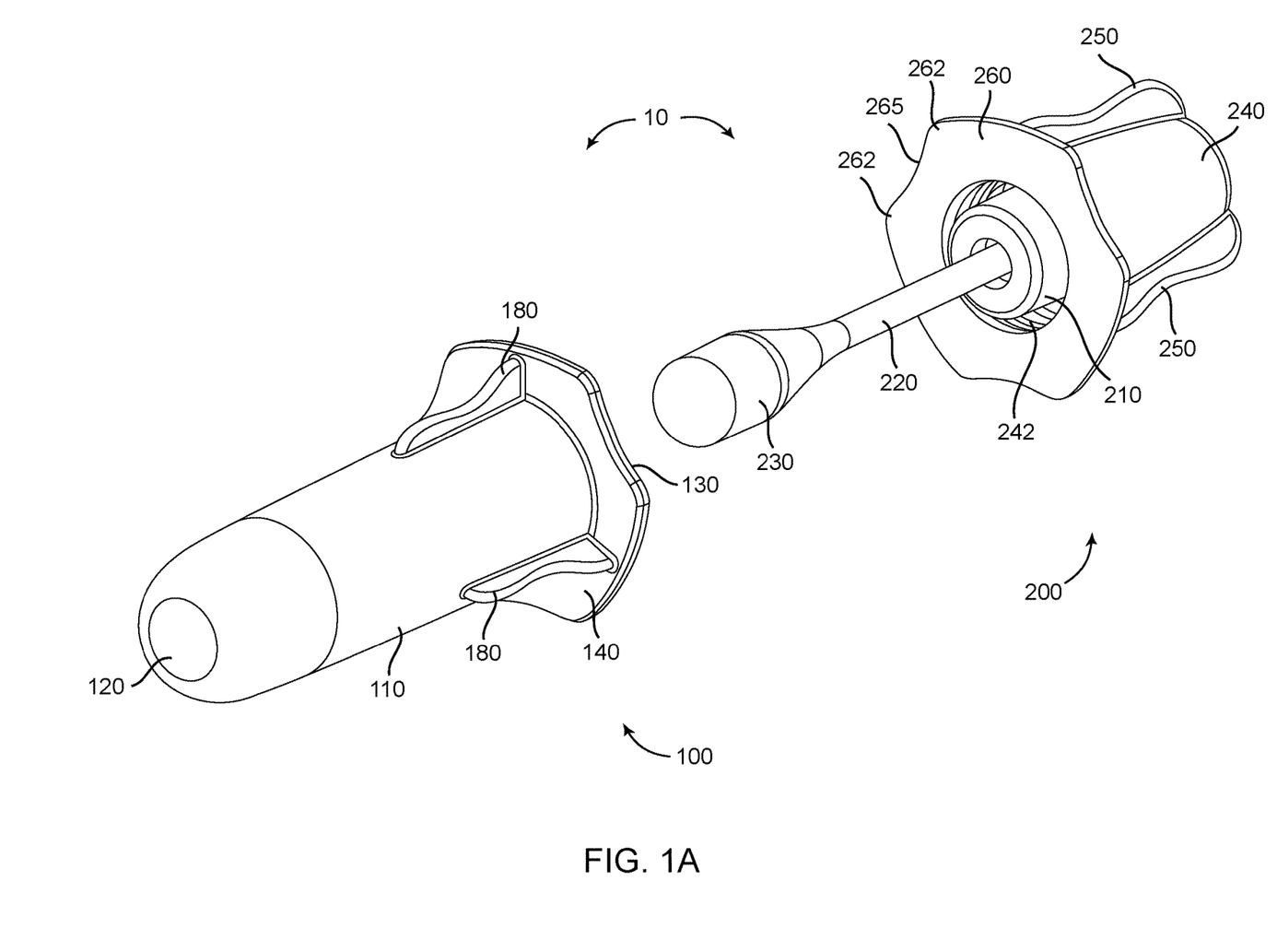
FIG. 1A shows a perspective view of the applicator with the receptacle section and handle section decoupled, in accordance with one embodiment of the invention.

With reference to FIG. 1A, an exemplary swab applicator 10 in accordance with one embodiment of the invention is disclosed. The applicator 10 comprises a receptacle section 100 and a detachable handle section 200. The handle section includes an end cap 240 that surrounds or encapsulates at least partially a stem seat 210. The end cap 240 may be rotatable. The stem seat 210 may be tapered and provides the surface for sealing when attached to the receptacle section 100. The stem seat 210 houses an applicator stem 220 affixed to its inner surface. For example, the stem 220 may be mechanically staked into the stem seat 210. The stem 220 has a swab 230 on its bottom end made of an absorbent material. In an embodiment, the stem 220 may have a uniform size throughout except at the end containing the swab 230 that is bigger. The end cap 240 may have a cylindrical body with a circular horizontal cross-section. The end cap 240 is fused into the stem seat 210. Alternately, it may be discrete. The bottom of the end cap 240 that is closer to the receptacle section has a collar 260. The collar 260 in the handle section acts as a basin to catch any drips of the liquid when the swab 230 is removed for use. The handle section collar 260 may have one or more notches 265 and a plurality of feet 262 that prevent rotation of the handle section and/or the applicator when resting on a flat surface. The collar 260 is optional. The notches 265 may be indents, cut-outs, protrusions, ridges, grooves or any other suitable mechanism to prevent rotation of the handle section and/or the applicator when resting on a flat surface. The end cap body has a plurality of ribs 250 on the exterior for an easy, natural-feeling and secure grip that also prevents rotation of the handle section and/or the applicator when resting on a flat surface by keeping the applicator elevated. The ribs 250 may be of any suitable shape such as curved or flat. The interior of the end cap body has female screw threads 242 or some other mechanism adapted for coupling or mating with the receptacle section, as discussed below.

Figure 1B:
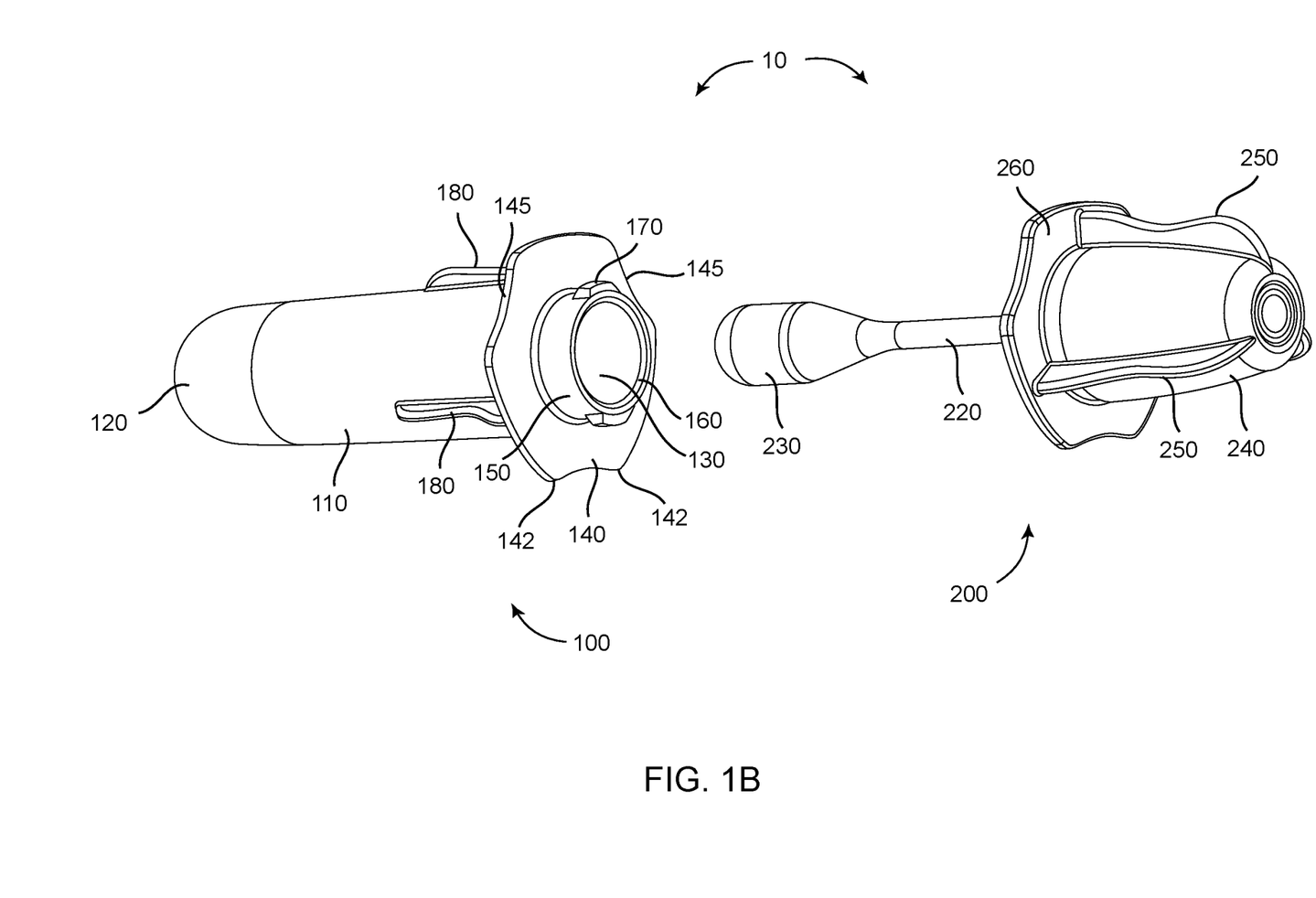
FIG. 1B shows another perspective view of the applicator with the receptacle section and handle section decoupled, in accordance with one embodiment of the invention.
Figure 2A:
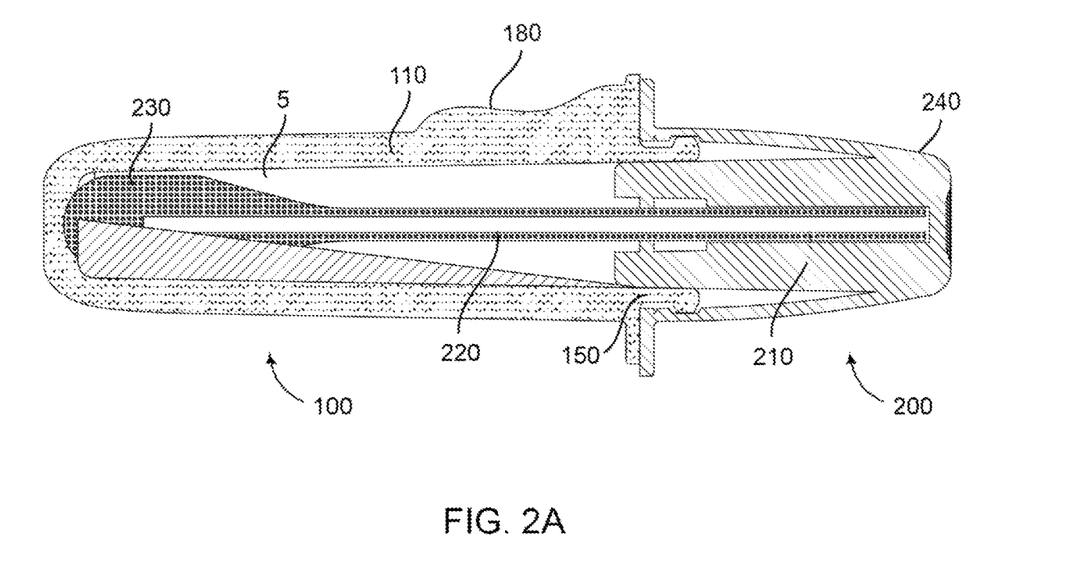
FIG. 2A shows a cross section of the applicator of FIG. 1A with the receptacle section and handle section coupled, in accordance with one embodiment of the invention.
Figure 2B:
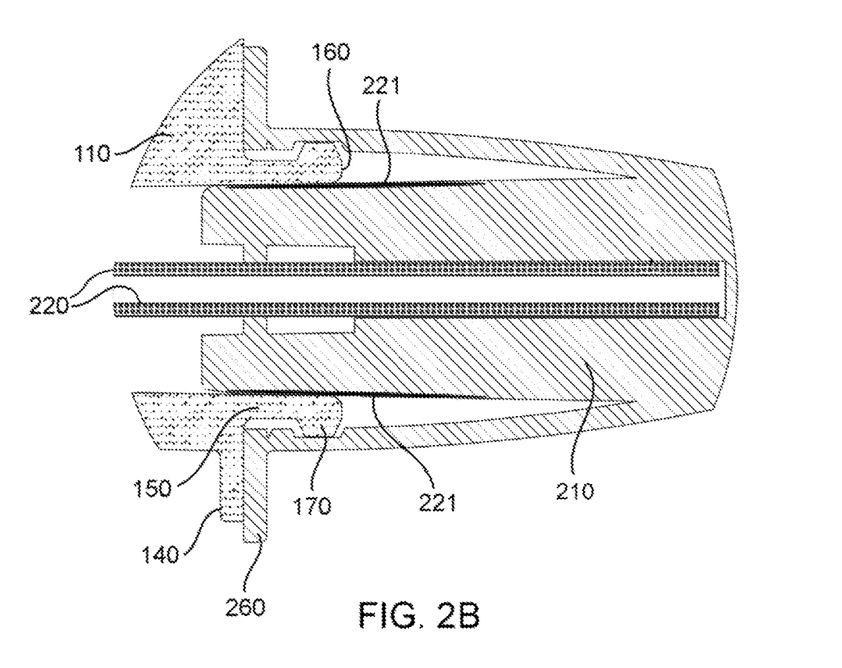
FIG. 2B shows a close-up view of the coupled area, where the seal is affected, of the applicator of FIG. 2A, in accordance with one embodiment of the invention.
Figure 2C:
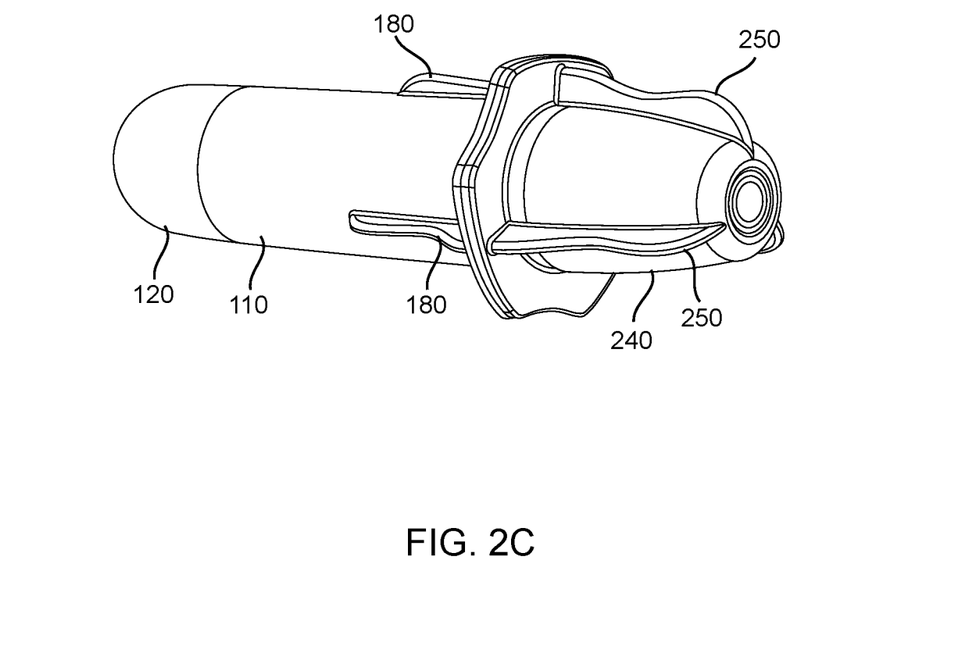
FIG. 2C shows an elevation view of the applicator of FIG. 1A with the two sections coupled, in accordance with one embodiment of the invention.
Figure 2D:
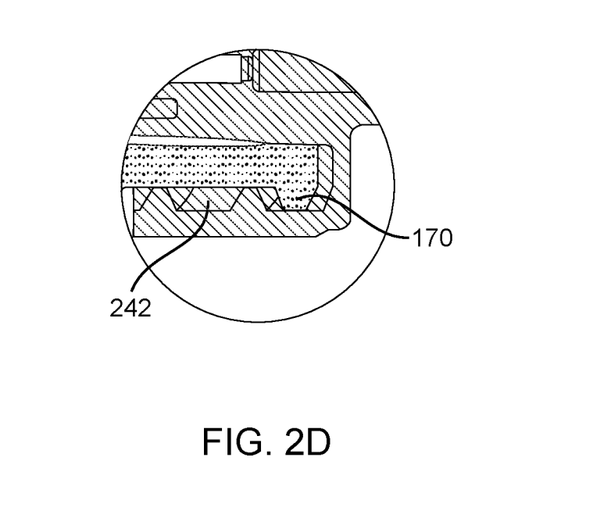
FIG. 2D shows a close-up view of the coupled area of the applicator of FIG. 2C showing the threads, in accordance with one embodiment of the invention.

With reference to FIG. 1B, the receptacle section 100 of the applicator 10 is shown. The receptacle section has a hollow body 110 with a narrow end 120 and a wider open end 130. The hollow body 110 may be conical or cylindrical with a circular horizontal cross-section. The portion containing the open end 130 includes a collar 140, a neck 150 and a rim 160. The receptacle section collar 140 has a plurality of feet 142 that allow the receptacle section to stand elevated when resting on a flat surface and prevent any spilling of the liquid inside the receptacle section. The collar 140 has one or more notches 145 corresponding to the feet that prevent rotation of the receptacle section and/or the applicator when resting on a flat surface. The notches 145 may be indents, cut-outs, protrusions, ridges, grooves or any other suitable mechanism to prevent rotation of the handle section and/or the applicator when resting on a flat surface. In one embodiment, the rim 160 may house male screw thread lugs 170 at the open end of the receptacle section that are adapted to mate or couple with the female screw threads 242 in the end cap body. In this embodiment, the thread lugs 170 engage the female threads 242 of the end cap. The thread may be a type known in the art such as a double start, right hand thread, which engages the female, on the handle section, and male, on the receptacle section, e.g., a luer taper. A close-up view of the threaded closure is shown in FIG. 2D. In one embodiment, there are at least two thread lugs 170. In another embodiment, there may be two or more thread lugs. Instead of threads, the handle and the receptacle sections may be secured together by other suitable connecting means, e.g., a latch. The neck may be tapered on the inner surface. The hollow body 110 may be cylindrical or any other suitable shape.

The hollow body of the receptacle section 100 is equipped with a plurality of ribs 180 at the open end starting from below the rim, for example, at the collar 140 or below the neck 150. The end cap 240 fits over the neck 150 when the receptacle section is coupled with the handle section. In one embodiment, the hollow body has four or more ribs 180. The ribs 180 extend from the collar 140 or neck 150 at least partway toward the closed end 120 of the receptacle section body. The ribs 180 prevent or inhibit any liquid contents of the hollow body 110 from leaking or spilling out because they keep the open end 130 of the body slightly elevated when the receptacle section 100 is laid flat on a surface, such as a table top. The ribs 180 also prevent rolling of the applicator when it is resting on a flat surface. In addition, the ribs 180 may provide a firm grip when a user grasps the receptacle section of the applicator to either move it, or to decouple or couple the receptacle section 100 and the handle section 200. The ribs 180 may be of any suitable shape such as flat or curved. The neck 150 may have one or more stiffening ribs 155 (shown in FIG. 4) to provide additional rigidity in the neck. The collar 140 and the stiffening ribs 155 are optional.

Figure 3A:
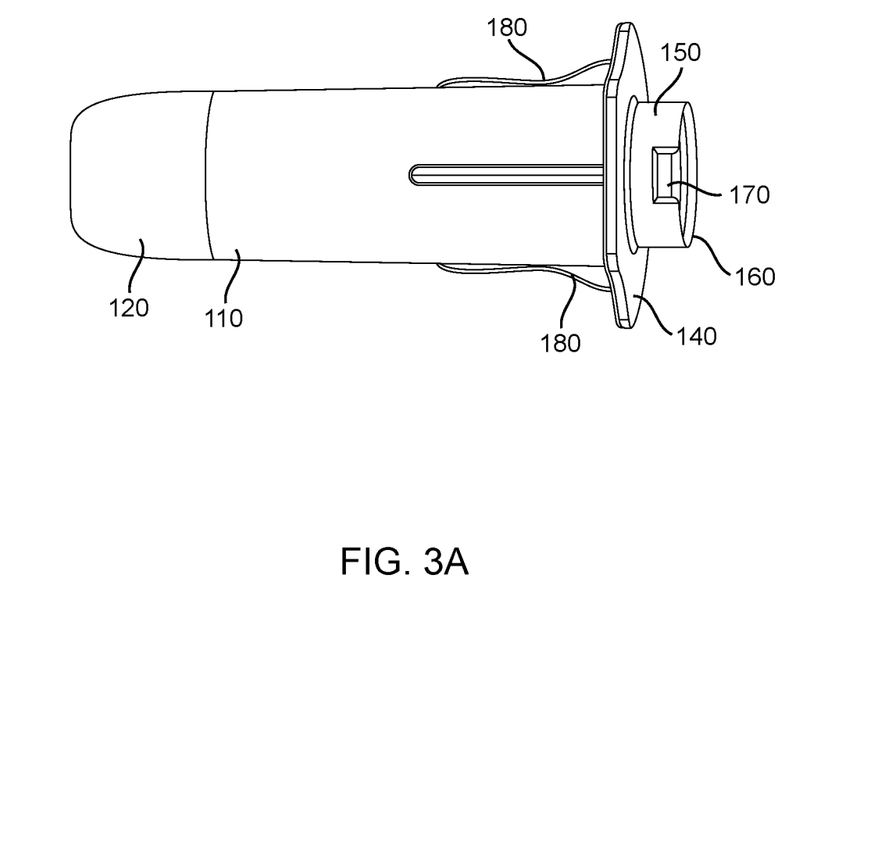
FIG. 3A is a perspective view of the receptacle section, shown without the swab, with the posterior end on the left and the anterior end on the right, in accordance with one embodiment of the invention.
Figure 3B:
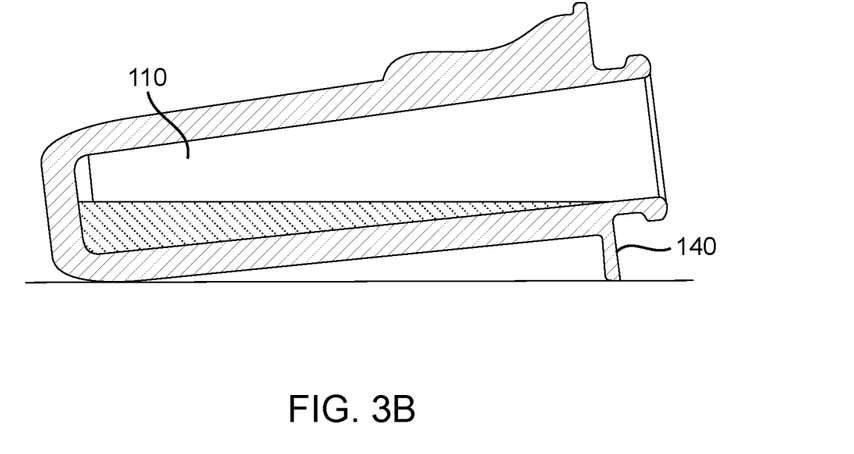
FIG. 3B is a perspective view of the receptacle section, shown with the fluid, resting on a flat surface, in accordance with one embodiment of the invention.

FIGS. 3A-3B show alternative views of the receptacle section 100. A perspective view of the receptacle section 100 is shown in FIG. 3A with the collar 140, neck 150, the rim 160 and the ribs 180. The receptacle section 100 is shown resting elevated on a horizontal flat surface such as a table top in FIG. 3B.

The handle section 200 mates or couples with the receptacle section 100 such that the stem seat 210 fits snugly through the neck 150 and across the hollow body 110, and the female threads 242 and male threads lugs 170 are engaged. The swab 230 contained on one end of the stem 220 is nested within the hollow body 110 of the receptacle section towards the closed end 120. The other end of the stem 220 rests in the stem seat 210. The end cap 240 fits over the neck 150 in this configuration. This nesting configuration is shown in cross section view of FIG. 2A. The applicator in this embodiment is filled with a pre-measured dose 5 contained within the cavity of the receptacle section body. An exterior view of the mated or coupled handle and receptacle sections is shown in FIG. 2C.

The stem seat 210 may be tapered with a narrower diameter at the anterior end that nests snugly into the neck 150, which may be correspondingly tapered on its interior. Alternately, the stem seat 210 and the neck 150 may be of uniform cross-section. An airtight seal is formed between the conical Luer tapered portions of the handle and receptacle sections. The angle of the taper is such that the parts would not fall apart without some applied force once they have been inserted into one another. This air-tight seal prevents any liquid in the receptacle section body from escaping after packaging of the applicator. The air-tight seal is formed by the snug contact and does not depend on compression or gravity. The threads or other connecting means serve to keep the receptacle and handle sections in contact with one another so as to maintain a snug fit. The seal is recloseable. A close-up view of the seal area is shown in FIG. 2B with the seal area 221 shown as shaded. The close conformity of the stem seat 210 to the neck and the tapering sides minimize the gap into which the contained liquid can seep. After the swab 230 is used, it may be inserted back into the receptacle body and the air-tight seal is formed again. The air-tight seal maintains a sterile environment in the receptacle section body, for example if the applicator is used to collect a tissue or excretion sample.

Figure 4:
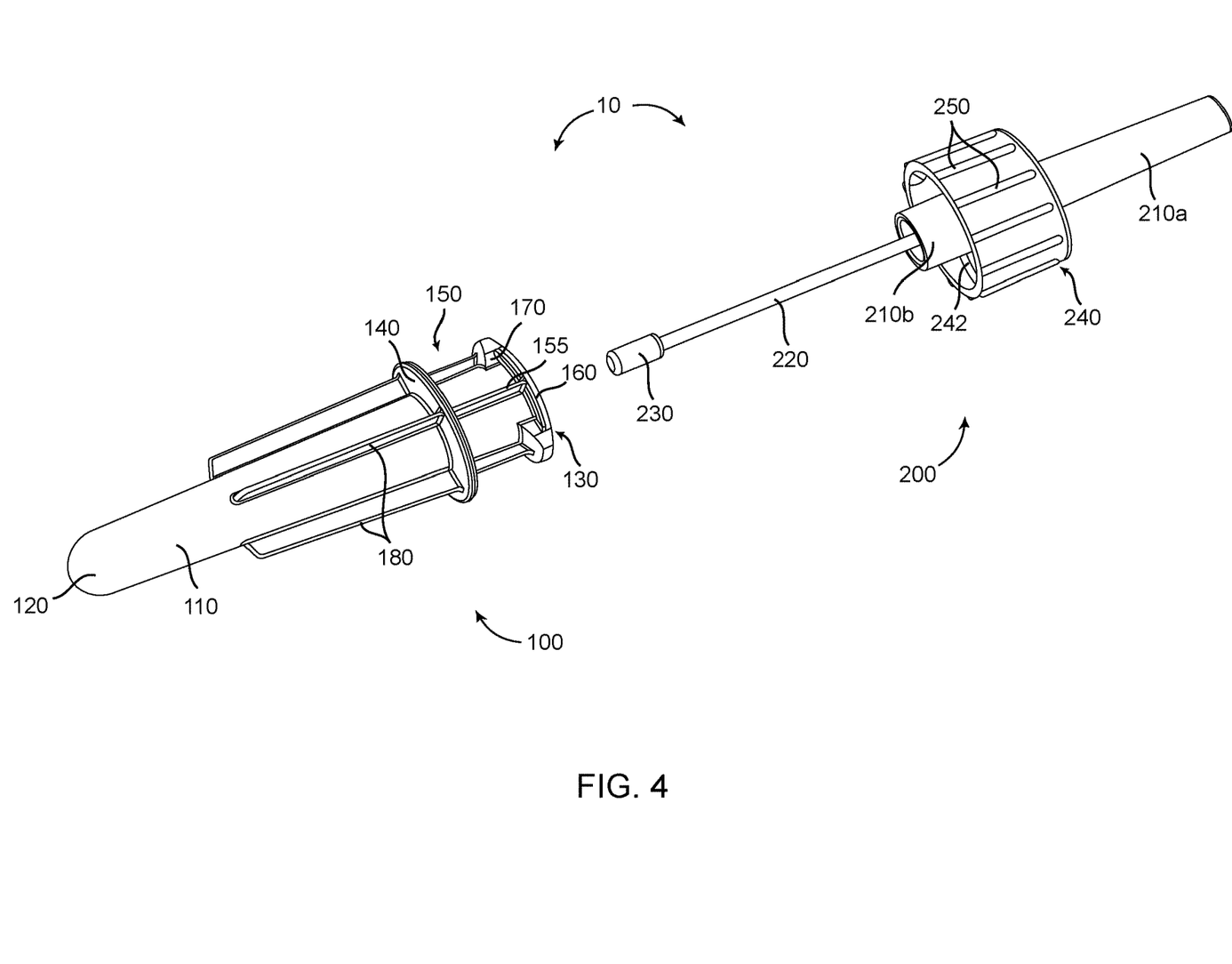
FIG. 4 shows a perspective view of the applicator with the receptacle section and handle section decoupled, in accordance with another embodiment of the invention.
Figure 5:
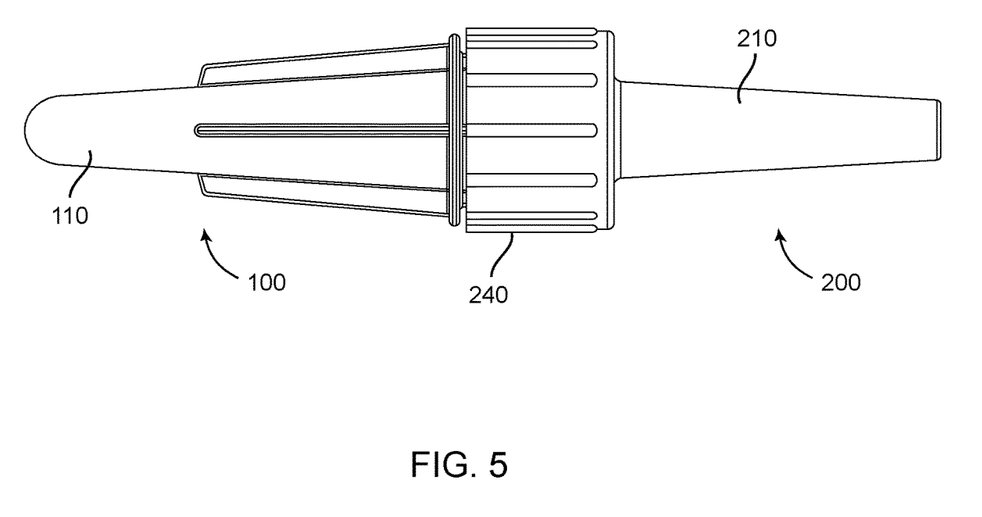
FIG. 5 shows an elevation view of the applicator of FIG. 4 with the two sections coupled, in accordance with another embodiment of the invention.

With reference to FIG. 4, an exemplary swab applicator 10 in accordance with another embodiment of the invention is disclosed. Here, the stem seat 210 extends beyond the end cap 240 and the end cap does not have a collar. The bottom 210b of the stem seat is below and/or under the end cap 240. The top section 210a of the stem seat 210 extends above the end cap 240 and allows a user another area to hold the handle section by. The end cap 240 serves as a drip shield and prevents any drips of the liquid when the swab 230 is removed for use. The end cap body has a plurality of flatter ridges 250 on the exterior for an easy, natural-feeling and secure grip that also prevents rotation of the handle section and/or the applicator when resting on a flat surface. The hollow body 110 of the receptacle section has a plurality of ribs 180 that prevent spilling of the liquid housed in the receptacle body. In this embodiment, the neck 150 of the receptacle section 100 has one or more stiffening ribs 155 to provide additional rigidity in the neck. The stiffening ribs are optional. The collar 140 of the receptacle section 100 is uniform without any cut-outs or feet. The collar is also optional. An exterior view of the mated or coupled handle and receptacle sections of this embodiment is shown in FIG. 5.

Figure 6:
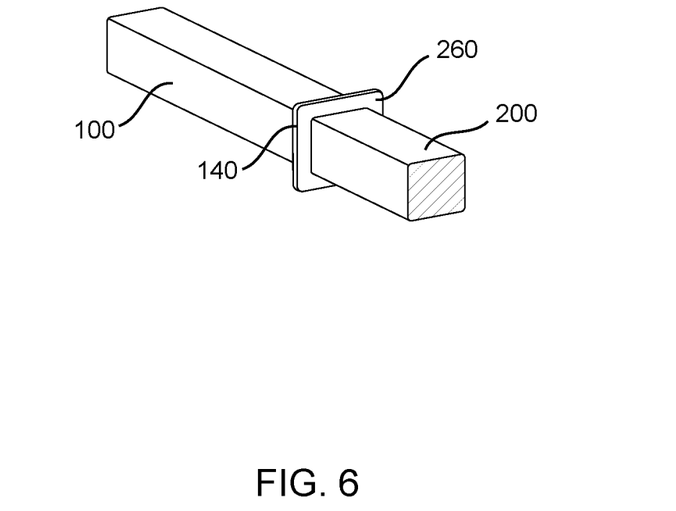
FIG. 6 shows an elevation view of the applicator with the receptacle section and the handle section coupled, in accordance with yet another embodiment of the invention.
Figure 7:
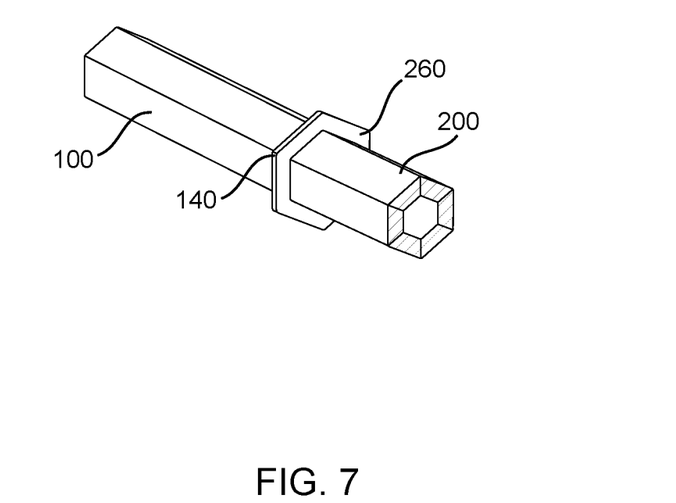
FIG. 7 shows an elevation view of the applicator with the receptacle and handle sections coupled, in accordance with another embodiment of the invention.

The anti-spill and anti-roll aspects of the improved swab applicator may be achieved by other features. For example, in yet another embodiment, the hollow body 110 of the receptacle section is polygonal in horizontal cross-section instead of, or in addition to, having a plurality of ribs 180. The polygonal cross-section such as rectangular, hexagonal, pentagonal, triangular etc. prevents rotation of the receptacle section when laying on the flat surface. The receptacle section may also have a collar 140. This allows the receptacle section to be elevated when resting on a flat surface and prevents spilling of the liquid contained in the receptacle body. The end cap 240 of the handle section may also be polygonal in horizontal cross-section instead of having a plurality of ridges or ribs 250. In addition, the handle section may also have a collar 260. FIG. 6 shows an applicator in a coupled configuration with the receptacle and handle sections having a rectangular horizontal cross-section. FIG. 7 shows an applicator in a coupled configuration with the receptacle and handle sections having a hexagonal horizontal cross-section.

A user may decouple the handle section 200 from the receptacle section 100 by grasping the exterior surface of the end cap 240 and rotating the handle section 200 relative to the receptacle section, to disengage the threads, and then pulling the handle section 200 away from the receptacle section 100 to break the air-tight seal and expose the swab for use.

In one embodiment, the applicator is packaged with the swab 230 nested in the hollow body 110 of the receptacle section. In this embodiment, the hollow body 110 acts as a reservoir that holds a liquid. The swab is impregnated with the liquid, e.g., medicine that is applied topically to a human or animal or for topical application into a body cavity of a human or animal. The liquid may be viscous. The applicator may be packaged with a pre-measured dose of medicine or liquid. The swab is packaged residing in the receptacle section 100. It is removed from the receptacle section for use and may be returned to the receptacle section after use. The swab applicator may be returned to the receptacle section following the topical application of the liquid and resealed by affecting the air-tight seal between the tapered sections of the receptacle and handle sections which are connected back by engaging the threads or other coupling means on the handle section and the receptacle section for a safe and clean disposal of the contaminated swab. For example, it may be coupled and resealed by nesting the handle section into the receptacle section and turning the handle section. The swab applicator together with any remaining liquid contents may be safely discarded in a resealed state following the topical application of the liquid such as a pharmaceutical composition.

In one embodiment, the receptacle section and the swab are sterile and the swab is decoupled from the receptacle section and used to collect a tissue sample or excretion from a body cavity of a human or an animal. Following collection, the swab applicator is returned to the coupled configuration for safe handling and holds the sterile samples for delivery to a laboratory for analysis, cell culture, or the like. The swab may be adapted to be inserted in a nose, ear, mouth, vagina, urethra or rectum of a human or an animal, i.e., in veterinary use. For example, the applicator could be used to deliver a drug into the nasal cavity by a user squeezing the side of a nostril while the swab is in the nasal cavity. For example, the applicator may be used to deliver drugs such as topical steroids for psoriasis. If the receptacle section of the applicator is filled with a pre-measured dose, the swab impregnated with the dose allows the dispensing and delivery of a precise amount of medicine or liquid to the target site. Thus, the improved swab applicator may be used to deliver any type of product that one would want to apply to a body part or surface and not have the user touch the product with his or her hands. It may also be used for forensics or to collect a sample or a fluid or scraping from a body cavity or wipe a surface for testing.

The swab 230 may be made of any suitable absorbent material such as cotton, rayon, polyester, and polyurethane. The swab applicator package may be manufactured by injection molding or other known techniques. It may be manufactured using thermoplastics, polypropylene, polyethylene and other suitable material. The receptacle section and/or the handle section may be manufactured in plastic or glass to increase product stability. The stem size, shape, and material may be modified in accordance with the viscosity of the liquid in such a way that the correct amount of composition or liquid remains attached to the swab.

It is to be understood that the above-described embodiments are only illustrative of the application of the principles of the present invention. The illustrative discussions above are not intended to be exhaustive or to limit the invention to the precise forms disclosed. Various modifications and alternative applications may be devised by those skilled in the art in view of the above teachings and without departing from the spirit and scope of the present invention and the following claims are intended to cover such modifications, applications, and embodiments.

The invention claimed is:

1. A sealed recloseable swab applicator comprising
   a. a stem wherein one end of the stem is attached to a swab;
   b. an applicator assembly comprising a handle section and a receptacle section, wherein the swab is nestable within the receptacle section, and wherein the applicator assembly has a decoupled and a coupled configuration;
   c. wherein the handle section comprises the stem and an endcap, wherein the other end of the stem is seated in a stem seat, the stem seat encapsulated at least partially by the end cap, and wherein the endcap comprises a body and a plurality of first ribs on the body, the ribs configured to prevent rolling, and wherein the endcap engages with the receptacle section;
   d. wherein the receptacle section comprises a hollow body with a closed end and an open end, wherein the open end has a neck, a rim and a plurality of second ribs on the hollow body, the ribs configured to prevent rolling;
   e. wherein in the coupled configuration, the handle section is in contact with the receptacle section and the stem seat fits snugly into the neck such that an air-tight seal is formed between the stem seat and the neck, and the swab and the stem are nested in the hollow body of the receptacle section; and
   f. wherein the handle section and receptacle section are detachable, such that the handle section and the receptacle section are in the decoupled configuration when detached, and the swab is exposed for use and wherein the handle section and the receptacle section may be re-closed with said air-tight seal.

2. The swab applicator of claim 1 further comprising a handle section collar and/or a receptacle section collar configured to prevent rolling.

3. The swab applicator of claim 2, wherein the handle section collar and/or the receptacle section collar has a plurality of feet.

4. The swab applicator of claim 1, wherein the receptacle section has four or more ribs.

5. The swab applicator of claim 1, wherein the receptacle section has two or more thread lugs adjacent to the rim of the receptacle section, and wherein the thread lugs engage female threads in the end cap.

6. The swab applicator of claim 1 further comprising a liquid contained within the hollow body of the receptacle section, the receptacle section coupled with the handle section.

7. The swab applicator of claim 1, wherein the applicator is packaged in the coupled configuration with a pre-measured dose of a liquid contained in the hollow body of the receptacle section and the swab is nested in the receptacle section and impregnated with the dose.

8. The swab applicator of claim 1, further comprising a liquid pharmaceutical composition impregnated into the swab.

9. The swab applicator of claim 6, wherein the receptacle section and the swab are sterile.

10. The swab applicator of claim 9, wherein the swab is adapted to be inserted in a nose, ear, mouth, vagina, urethra or rectum of a human or animal.

11. A sealed recloseable swab applicator comprising
    a. a stem wherein one end of the stem is attached to a swab;
    b. an applicator assembly comprising a handle section and a receptacle section, wherein the swab is nestable within the receptacle section, and wherein the applicator assembly has a decoupled and a coupled configuration;
    c. wherein the handle section comprises the stem and an endcap, wherein the other end of the stem is seated in a stem seat, the stem seat encapsulated at least partially by the end cap, and wherein the endcap engages with the receptacle section;
    d. wherein the receptacle section comprises a hollow body with a closed end and an open end, wherein the open end has a neck and a rim, wherein the hollow body has a polygonal horizontal cross-section configured to prevent rolling;
    e. wherein in the coupled configuration, the handle section is in contact with the receptacle section and the stem seat fits snugly into the neck such that an air-tight seal is formed between the stem seat and the neck, and the swab and stem are nested in the hollow body of the receptacle section; and
    f. wherein the handle section and receptacle section are detachable, such that the handle section and the receptacle section are in the decoupled configuration when detached, and the swab is exposed for use and wherein the handle section and the receptacle section may be re-closed.

12. The swab applicator of claim 11 further comprising a receptacle section collar configured to prevent rolling.

13. The swab applicator of claim 12 further comprising a handle section collar configured to prevent rolling.

14. The swab applicator of claim 1, wherein the receptacle section and the swab are sterile.

15. The swab applicator of claim 2, wherein the receptacle section and the swab are sterile.

16. The swab applicator of claim 3, wherein the receptacle section and the swab are sterile.

17. The swab applicator of claim 4, wherein the receptacle section and the swab are sterile.

18. The swab applicator of claim 5, wherein the receptacle section and the swab are sterile.

19. A sealed recloseable swab applicator comprising
    a. a stem wherein one end of the stem is attached to a swab;
    b. an applicator assembly comprising a handle section and a receptacle section, wherein the swab is nestable within the receptacle section, and wherein the applicator assembly has a decoupled and a coupled configuration;
    c. wherein the handle section comprises the stem and an endcap, wherein the other end of the stem is seated in a stem seat, the stem seat is encapsulated at least partially by the end cap, and wherein the endcap engages with the receptacle section;
    d. wherein the receptacle section comprises a hollow body with a closed end and an open end, wherein the open end has a neck, a rim and a plurality of ribs on the hollow body, the ribs configured to prevent rolling;
    e. wherein in the coupled configuration, the handle section is in contact with the receptacle section and the stem seat fits snugly into the neck such that an air-tight seal is formed between the stem seat and the neck and the swab and stem are nested in the hollow body of the receptacle section;

f. wherein the handle section and receptacle section are detachable, such that the handle section and the receptacle section are in the decoupled configuration when detached, and the swab is exposed for use; and g. wherein the handle section and the receptacle section may be re-closed with an air-tight seal.

20. The swab applicator of claim 19 further comprising a receptacle section collar having a plurality of feet, the collar configured to prevent rolling and to prevent spilling of liquid contained within the receptacle body.

* * * * *